United States Patent
Greenwood et al.

(10) Patent No.: US 11,587,423 B2
(45) Date of Patent: Feb. 21, 2023

(54) FALL VALIDATION WITH PRIVACY-AWARE MONITORING

(71) Applicant: Healthcare Integrated Technologies Inc., Knoxville, TN (US)

(72) Inventors: Kenneth M. Greenwood, Davenport, FL (US); Scott Michael Boruff, Knoxville, TN (US); Jurgen Klaus Vollrath, Sherwood, OR (US)

(73) Assignee: Healthcare Integrated Technologies, Inc., Knoxville, TN (US)

( * ) Notice: Subject to any disclaimer, the term of this patent is extended or adjusted under 35 U.S.C. 154(b) by 2 days.

(21) Appl. No.: 17/390,775

(22) Filed: Jul. 30, 2021

(65) Prior Publication Data

US 2022/0036716 A1 Feb. 3, 2022

Related U.S. Application Data

(60) Provisional application No. 63/103,415, filed on Aug. 3, 2020.

(51) Int. Cl.
G08B 21/04 (2006.01)
G06T 13/40 (2011.01)
A61B 5/11 (2006.01)
G06N 3/02 (2006.01)

(52) U.S. Cl.
CPC .......... *G08B 21/043* (2013.01); *A61B 5/1117* (2013.01); *G06N 3/02* (2013.01); *G06T 13/40* (2013.01); *G08B 21/0469* (2013.01); *G08B 21/0476* (2013.01)

(58) Field of Classification Search
CPC .............. G08B 21/043; G08B 21/0469; G08B 21/0476; G08B 13/19686; A61B 5/1117; G06N 3/02; G06T 13/40
See application file for complete search history.

(56) References Cited

U.S. PATENT DOCUMENTS

| | | | | |
|---|---|---|---|---|
| 7,366,359 B1* | 4/2008 | Davey | ................... | G06V 20/52 346/143 |
| 10,832,060 B2* | 11/2020 | Lee | ........................ | G06N 20/10 |
| 11,170,295 B1* | 11/2021 | Carmichael | .......... | G06N 3/0454 |
| 2003/0058111 A1* | 3/2003 | Lee | .................. | G08B 13/19641 348/E7.086 |
| 2003/0058341 A1* | 3/2003 | Brodsky | ................ | G06V 20/52 348/E7.086 |
| 2003/0139902 A1* | 7/2003 | Geib | ....................... | C02F 1/441 702/181 |
| 2005/0159653 A1* | 7/2005 | Iijima | .................. | A61B 5/0002 128/903 |
| 2008/0267403 A1* | 10/2008 | Boult | .................... | H04L 9/0894 380/255 |
| 2011/0043630 A1* | 2/2011 | McClure | .......... | G08B 13/19602 348/143 |
| 2013/0082837 A1* | 4/2013 | Cosentino | ............ | G08B 25/016 340/539.12 |
| 2015/0213702 A1* | 7/2015 | Kimmel | .................... | G06T 7/20 382/103 |
| 2015/0339736 A1* | 11/2015 | Bennett | .............. | G06Q 30/0278 705/306 |

(Continued)

*Primary Examiner* — Curtis J King
(74) *Attorney, Agent, or Firm* — Jurgen Vollrath

(57) ABSTRACT

A method and system for detecting a person falling, confirming a potential fall, and taking action to mitigate the effects of a fall.

13 Claims, 4 Drawing Sheets

(56) References Cited

U.S. PATENT DOCUMENTS

| | | | |
|---|---|---|---|
| 2016/0183847 A1* | 6/2016 | Pae | A61B 5/1117 |
| | | | 600/595 |
| 2016/0210838 A1* | 7/2016 | Yan | G08B 25/001 |
| 2018/0342081 A1* | 11/2018 | Kim | G06T 7/254 |
| 2019/0090786 A1* | 3/2019 | Kim | G06N 3/08 |
| 2020/0090484 A1* | 3/2020 | Chen | G06K 9/6257 |
| 2020/0211154 A1* | 7/2020 | Ng | A61B 5/7275 |
| 2020/0342737 A1* | 10/2020 | Pham | G06F 3/011 |
| 2021/0035437 A1* | 2/2021 | Zhang | G06V 20/52 |
| 2021/0195034 A1* | 6/2021 | Ishibashi | H04N 1/0009 |
| 2021/0256829 A1* | 8/2021 | Ten Kate | G08B 29/16 |
| 2022/0103760 A1* | 3/2022 | Hastings | H04N 5/232945 |

* cited by examiner

FALL VALIDATION WITH PRIVACY-AWARE MONITORING

FIELD OF THE INVENTION

The present invention relates to fall detection in, especially for the elderly and people living alone.

BACKGROUND OF THE INVENTION

People in old age homes, care facilities, hospitals, or who are living alone are at greater risk when it comes to falling. Not only are the elderly and infirm more likely to fall, but the consequences are also more severe, especially when there is no one around to provide help in a timeous manner. Wearable fall detectors, like the FitBit wristwatch and Life Alert pendant have limited accuracy in identifying when a user has fallen. In many instances, the fall may be a gradual lowering to the ground as a user feels dizzy or is starting to pass out. In these situations, accelerometer-based devices are extremely unreliable in detecting falls. Also, insofar as a user has passed out, they may not be in a position to notify emergency response teams or family members to alert them that there is an emergency. Pendants on a lanyard have also been known to become a choking hazard.

Studies have also shown that many users take their wearables off at night when they go to bed, thus leaving them exposed if they have to get up in the middle of the night or if they forget to put the wearable device back on again the next morning.

The present invention seeks to address these shortcomings.

SUMMARY OF THE INVENTION

According to the invention, there is provided a fall detector, comprising an image capture device, a microphone, and a processor connected to a memory that includes machine-readable code defining an algorithm for controlling the image capture device and microphone to monitor a person for purposes of detecting falls, wherein the image capture device is adapted to capture only select information, and the algorithm is configured to identify flagging events based on falls detected by the image capture device, and to capture sound data from the microphone to supplement information not captured by the image capture device and to corroborate potential falls detected by the image capture device.

Data not captured by the image capture device may include dead zones not covered by the image capture device, and privacy regions designated in the algorithm as private areas, which are obscured.

The image capture device may include one or more of a video camera, a camera operating in a frequency range outside the visual spectrum that inherently limits image quality, a digital camera system where the pixel count is kept low enough to limit image quality to protect privacy, and a radar or sonar device.

The processor may be configured to compare verbal and non-verbal input from the microphone to pre-recorded sounds of people falling including exclamations by third parties or by the person being monitored, which are associated with a falling event, in order to corroborate a potential fall detected by the image capture device.

The algorithm may include an artificial intelligence (AI) system trained on fall image data to identify falls and potential falls. The AI system may parse the image data captured by the image capture device in order to identify trigger events that require corroboration by a second data source, and flagging events that warrant notifying a third-party.

The second data source may comprise sound data from the microphone for the same time frame.

The fall detector may further comprise a speaker connected to the processor, wherein the algorithm is configured to generate a message to the person being monitored, in the event of a fall or potential fall being detected by the image capture device or microphone, wherein the message may comprise one or more of: a consoling message in the event of a fall being detected to console the person that help is on the way, and a confirmation message in the event of a potential fall to verify that the person did fall, and using the microphone to capture any response for purposes of corroborating data from the image capture device or microphone.

Further, according to the invention, there is provided a fall detector comprising a video camera to capture video data, a processor, and a memory connected to the processor, wherein the memory includes machine-readable code adapted to parse the video data to identify fall events, to obfuscate the video data, and to keep a record of at least one of the video data and the obfuscated video data.

The fall detector may further comprising a motion detector, wherein the machine-readable code is adapted to keep a record of the video data or obfuscated video data only when motion is detected.

The machine-readable code may be adapted to generate an avatar of each human being captured or recorded by the video camera.

Still further, according to the invention, there is provided a method of enhancing the safety of a user in a dwelling, comprising monitoring the user for falls in the dwelling by capturing image and sound data, and corroborating the image data and the sound data in the event of a suspected fall, respectively with sound data and image data captured over a corresponding time frame.

The method may further include corroborating a suspected fall by querying the user about the user's condition.

DETAILED DESCRIPTION OF THE INVENTION

Figure 1:
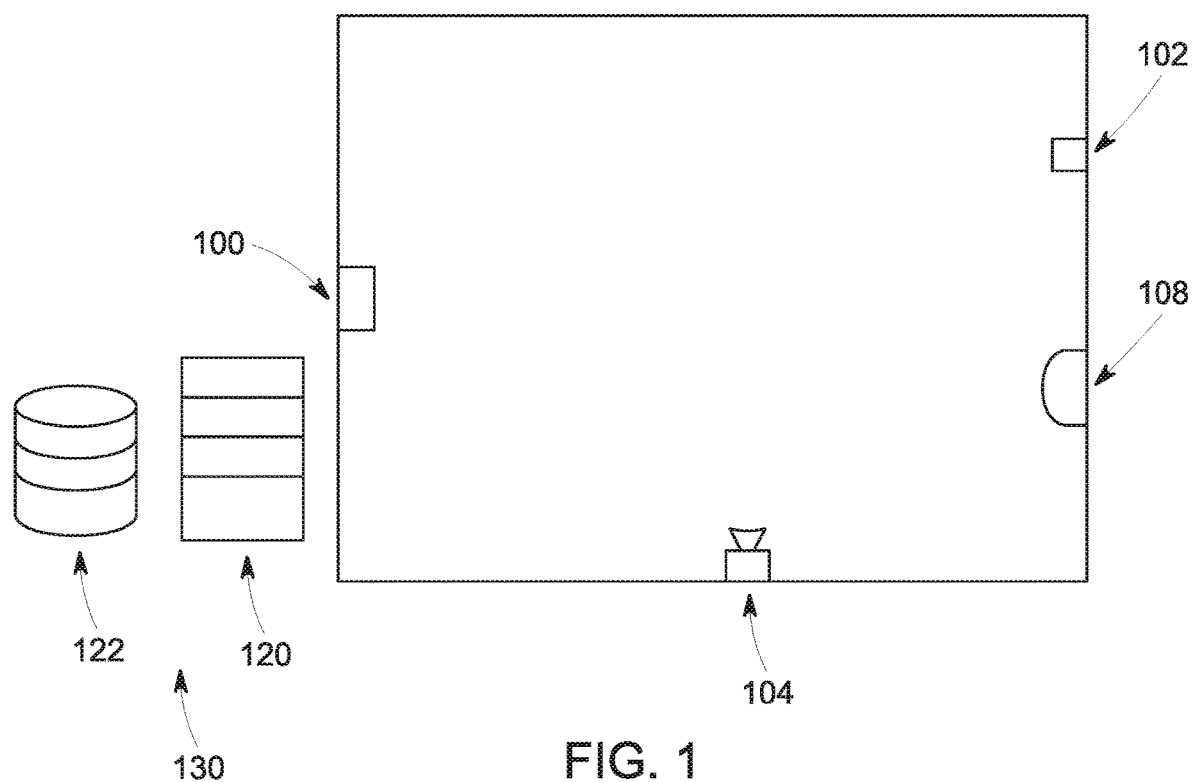
FIG. 1 is a depiction of one embodiment of a system of the invention.

One embodiment of an interactive communication platform of the invention is shown in FIG. 1. It includes a image capture device 100 mounted on a wall in a user's apartment, a microphone 102 for capturing verbal and non-verbal sound information, and a speaker 104 for verbally addressing the user.

The image capture device 100, microphone 102, and speaker 104 are connected to a processor, which is not shown but is included in the housing for the speaker 104.

The image capture device 100 and microphone 102 are communicatively connected to the processor by means of short-range wireless connections, in this case, Bluetooth.

The image capture device 100 and microphone 102 in this embodiment are implemented to always be on, so as to capture all activities of the user. Instead, the image capture device 100 (which in one implementation comprises an RGB video camera) may include a motion detector and may only be activated when movement is detected by the motion detector, or when the microphone 102 turns on. Similarly, the microphone 102 may only turn on when a sound is detected by the microphone or the image capture device 100 turns on.

Both the image capture device 100 and microphone 102 can therefore pick up emergencies such as the user falling. The image capture device 100 will detect when a user drops to the ground, either slowly or suddenly, while the microphone 102 will pick up thuds or percussion sounds associated with a fall, or verbal exclamations by a person, indicative of a fall, even if the user is outside the viewing field of the image capture device 100. In some instances the data from one device may identify an anomaly in the visual or sound data but be insufficient to clearly define the anomaly as a triggering event (also referred to herein as an emergency event, or flagging event). In such cases corroboration by a second device for the same or a related time-frame may serve to provide the necessary evidence to elevate an anomaly to an event, requiring third party intervention. For instance, both devices could pick up anomalies or flagging events such as a person falling, allowing the information of one device, e.g., the image capture device 100 to be corroborated against that of the other device (in this case the microphone).

The system of the present embodiment also includes a memory (not shown) connected to the processor and configured with machine-readable code defining an algorithm for analyzing the data from the image capture device 100 and microphone 102 and comparing it to a database of previously captured image data of people falling, and to previously captured sounds (both verbal exclamations and non-verbal sounds) associated with persons falling. In the case of verbal sounds, e.g. exclamations, the previously captured verbal data is preferably based on verbal data captured from the user, in order to ensure comparison with the user's actual voice, with its distinct frequency, timbre, and other vocal attributes. The database information may be stored in a section of the memory or a separate memory.

In this embodiment some of the processing is done locally, as it relates to the comparison of data from the image capture device 100 and microphone 102 to the previously captured data. The present embodiment also does some of the processing remotely by including a radio transceiver (not shown), which in this embodiment is implemented as a WiFi connection to a server 120

In one embodiment, the anomaly analysis is implemented in software and involves logic in the form of machine readable code defining an algorithm or implemented in an artificial intelligence (AI) system, which is stored on a local or remote memory (as discussed above), and which defines the logic used by a processor to perform the analysis and make assessments.

Figure 2:
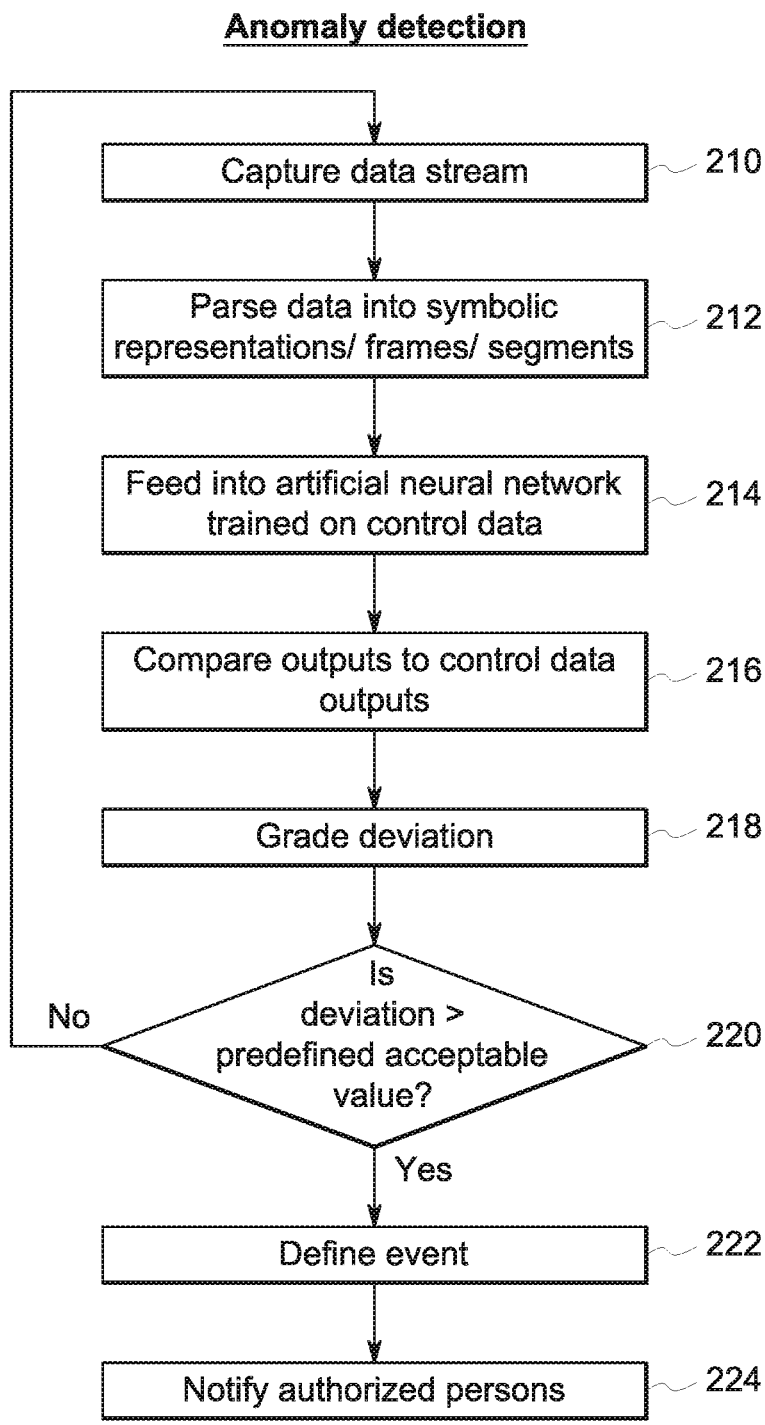
FIG. 2 is a flow chart defining the logic of one embodiment of an anomaly detection algorithm implemented in an AI system.

One such embodiment of the logic based on grading the level of the anomaly, is shown in FIG. 2, which defines the analysis based on sensor data that is evaluated by an Artificial Intelligence (AI) system, in this case an artificial neural network. Data from a sensor is captured (step 210) and is parsed into segments (also referred to as symbolic representations or frames) (step 212). The symbolic representations are fed into an artificial neural network (step 214), which has been trained based on control data (e.g. similar previous events involving the same party or parties or similar third-party events). The outputs from the AI are compared to outputs from the control data (step 216) and the degree of deviation is graded in step 218 by assigning a grading number to the degree of deviation. In step 220 a determination is made whether the deviation exceeds a predefined threshold, in which case the anomaly is registered as an event (step 222) and one or more authorized persons is notified (step 224)

Figure 3:
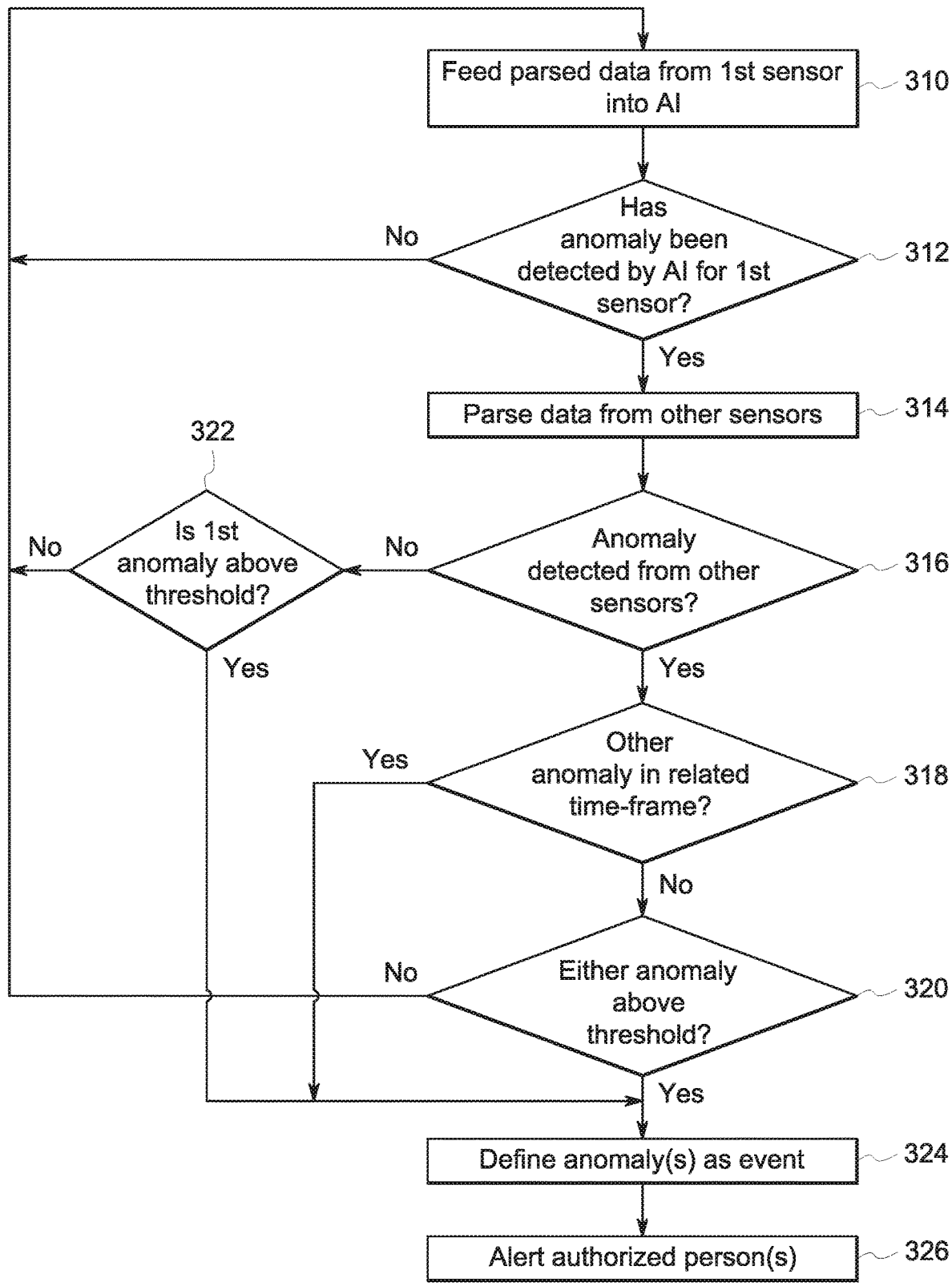
FIG. 3 is a flow chart defining the logic of one embodiment of an anomaly detection and corroboration algorithm implemented in an AI system.

Another embodiment of the logic in making a determination, in this case, based on grading of an anomaly and/or corroboration between sensors is shown in FIG. 3.

Parsed data from a first sensor is fed into an AI system (step 310). Insofar as an anomaly is detected in the data (step 312), this is corroborated against data from at least one other sensor by parsing data from the other sensors that are involved in the particular implementation (step 314). In step 316 a decision is made whether any of the other sensor data shows up an anomaly, in which case it is compared on a time scale whether the second anomaly is in a related time frame (which could be the same time as the first sensor anomaly or be causally linked to activities flowing from the first sensor anomaly) (step 318). If the second sensor anomaly is above a certain threshold deviation (step 320) or, similarly, even if there is no other corroborating sensor data, if the anomaly from the first sensor data exceeds a threshold deviation (step 322), the anomaly captured from either of such devices triggers an event (step 324), which alerts one or more authorized persons (step 326).

The server 120 also includes a database 122 for storing data from the image capture device 100 and microphone 102. In one embodiment it will capture and retain for a period of time, all of the data received from the image capture device 100 and microphone 102. In another embodiment it will only retain data associated with a flagging event identified by the local processor, where the local processor has determined that at least one of the two sensors (image capture device 100 or microphone 102) has picked up data that corresponds to previously captured data associated with a fall.

In order to protect the privacy of the person or people being monitored, the logic in the memory connected to the local processor may be configured to obfuscate the video data in order to create a blurred set of images of the retained image data. The logic may also use the parsed video data to generate avatars of the person or people being monitored. It will be appreciated that in a simplified embodiment, the system may avoid the need of the microphone, and rely purely on the video data to identify falls. In such an embodiment it is critical to protect the privacy of the people being monitored especially when monitoring the bathroom. In addition to obfuscating the image data, the logic in the memory may define blacked-out privacy regions, e.g., the toilet. Also, the logic may be configured to only capture video data when a flagging event is identified.

In the broader embodiment that includes a microphone, the database 122 also captures and retains sound files of non-verbal data associated with trigger events. In this embodiment the memory associated with the local processor includes logic for comparing non-verbal sounds received from the microphone to previously recorded non-verbal sounds, e.g. thuds corresponding to a person falling, thereby defining a falling event, which may trigger additional action, as is discussed further below.

In another embodiment, all of the processing is done remotely, in which case the database 122 includes previously captured image data, non-verbal sounds and voice-prints obtained from the user to define falling events.

Server 120 also includes a memory configured with machine readable code to define an artificial intelligence (AI) system (also referred to herein as an AI network), depicted by reference numeral 130. The AI system 130, inter alia, processes flagging events from one device (e.g. image capture device 100) and compares them with the other device (e.g., microphone 102) to corroborate a falling event for a corresponding time-frame.

As discussed above, the database 122, in one embodiment, includes previously captured image data, non-verbal sound data, and voice-prints, which allows the AI system to compare information captured by the image capture device 100 and microphone 102 to the previously captured data to identify falling events.

Certain potential falling events may require a closer view of the user, and the AI system is configured to identify the location of the user and zoom in on the user to capture a closer view of the person's body position or facial features. The facial expressions may provide information that the person is in pain or stress, based on comparisons to previously captured facial images of the user under different situations. The facial expression may include the configuration of the mouth, the creases formed around the mouth, creases along the forehead and around the eyes, the state of the eyes, and the dilation of the pupils.

The speaker 104 is integrated with the AI system to define a voice-bot for interacting with the user. It is configured to engage the user in conversation: in response to a fall event or potential fall event in order to gather additional information for purposes of corroborating or validating a fall event.

Upon the occurrence of a potential fall event, e.g. when the image capture device 100 or microphone 102 picks up data corresponding to a fall, data from the one device may be used to corroborate data from the other device. In the absence of sufficient information to warrant elevating the event to a trigger event that warrants third party intervention, the devices are configured to acquire additional information.

The image capture device, as discussed above, may zoom in on the user to assess body posture and facial features, and compare these to the image data in the database.

In response to image data suggesting a possible fall event, or in response to a verbal exclamation or non-verbal sound (e.g., one suggesting a falling event based on comparisons to previously captured sound files), the speaker 104 may engage the user in conversation, e.g., asking: "Are you alright?" or "Is everything alright?".

Thus, in addition to the visual parameters (body posture and facial features captured by the image capture device 100), this allows a more detailed analysis of the speech-related parameters (as captured by the microphone 102).

In this embodiment, the voice signals are analyzed for intonation, modulation, voice patterns, volume, pitch, pauses, speed of speech, slurring, time between words, choice of words, and non-verbal utterances.

By analyzing the speech patterns of the verbal response or the lack of a response, the AI system may elevate a possible falling event to an emergency or trigger event, initiating a call to one or more persons in the database 122. For this purpose, the database 122 may include contact details of administrative staff responsible for the user, a physician or medical facility associated with the user, an emergency response entity, or a family member or emergency contact associated with the user, etc. The AI system, in this embodiment is configured to automatically contact one or more emergency numbers, depending on the situation, or connect the user with a contact person.

Also, the AI system may use the voice signals and images captured from a specific user, which are associated with one or more corroborated falling events, to refine the voice-prints and image data for the specific user. Thus, it becomes continuing teaching data for the AI system.

Similarly, the user may actively initiate a conversation or other interaction with the voice-bot by requesting an action (e.g. to connect the user by video or audio link with a specified person or number).

Figure 4:
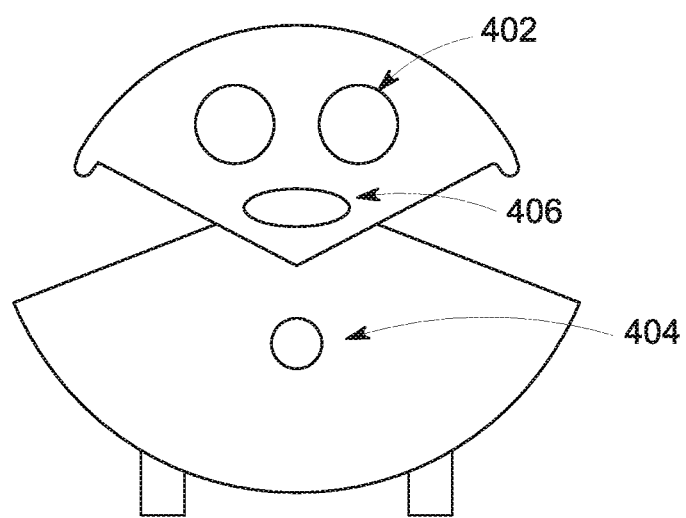
FIG. 4 is a depiction of part of another embodiment of a system of the invention.

Another embodiment of the present system is shown in FIG. 4, wherein the AI system is implemented as a robot 400, which, in this embodiment is a mobile robot allowing it to approach the user for closer inspections, or to detect muffled or low-volume sounds, such as breathing or mumbling by the user.

This embodiment incorporates a image capture device 402, microphone 404, and speaker 406 in the robot 400. As in the FIG. 1 embodiment, the robot 400 may include both a processor for local processing of data captured by the image capture device 402 and microphone 404, as well as a transceiver (cell phone or internet based radio transceiver) to communicate with a remote server such as the server 120 discussed above with respect to FIG. 1.

While the present invention has been described with respect to specific embodiments, it will be appreciated that the invention could be implemented in different manners, with additional sensors and communication devices, and with differently configured processing of the data captured by the sensors, without departing from the scope of the invention.

What is claimed is:

1. A fall detector, comprising
an image capture device,
a microphone, and
a processor connected to a memory that includes machine-readable code defining an algorithm for controlling the image capture device and microphone to monitor a person for purposes of detecting falls, wherein the image capture device is adapted to capture only select information, and the algorithm is configured to identify flagging events based on falls detected by the image capture device, and to capture sound data from the microphone to supplement information not captured by the image capture device and to corroborate potential falls detected by the image capture device.

2. The fall detector of claim 1, wherein the data not captured by the image capture device includes dead zones not covered by the image capture device, and privacy regions designated in the algorithm as private areas, which are obscured.

3. The fall detector of claim 1, wherein the image capture device includes one or more of a video camera, a camera operating in a frequency range outside the visual spectrum that inherently limits image quality, a digital camera system where the pixel count is kept low enough to limit image quality to protect privacy, and a radar or sonar device.

4. The fall detector of claim 1, wherein the processor is configured to compare verbal and non-verbal input from the microphone to pre-recorded sounds of people falling including exclamations by third parties or by the person being monitored, which are associated with a falling event, in order to supplement information not captured by the image capture device and to corroborate a potential fall detected by the image capture device.

5. The fall detector of claim 4, wherein the algorithm includes an artificial intelligence (AI) system trained on fall image data to identify falls and potential falls.

6. The fall detector of claim 5, wherein the AI system parses the image data captured by the image capture device and identifies trigger events that require corroboration by a second data source, and flagging events that warrant notifying a third-party.

7. The fall detector of claim 6, wherein the second data source comprises sound data from the microphone for the same time frame.

8. The fall detector of claim 7, further comprising a speaker connected to the processor, wherein the algorithm is configured to generate a message to the person being monitored, in the event of a fall or potential fall being detected by the image capture device or microphone.

9. The fall detector of claim 8, wherein the message comprises one or more of: a consoling message in the event of a fall being detected that help is on the way, and a confirmation message in the event of a potential fall to verify that the person did fall, and using the microphone to capture any response for purposes of corroborating data from the image capture device or microphone.

10. A fall detector comprising
a video camera to capture video data,
a processor, and
a memory connected to the processor, wherein the memory includes-machine-readable code adapted to parse the video data to identify fall events, and the machine-readable code is adapted to generate an avatar of each human being captured or recorded by the video camera.

11. The fall detector of claim 10, further comprising a motion detector, wherein the machine-readable code is adapted to keep a record of the video data or obfuscated video data only when motion is detected.

12. A method of enhancing the safety of a user in a dwelling, comprising
monitoring the user for falls in the dwelling by capturing image and sound data, and
corroborating the image data and the sound data in the event of a suspected fall, respectively with sound data and image data captured over a corresponding time frame.

13. The method of claim 12, further comprising corroborating a suspected fall by querying the user about the user's condition.

* * * * *